(12) United States Patent
Vogt et al.

(10) Patent No.: US 10,485,598 B2
(45) Date of Patent: Nov. 26, 2019

(54) TENSIONED OPENING DEVICE FOR MONOMER CONTAINER

(71) Applicant: HERAEUS MEDICAL GMBH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 481 days.

(21) Appl. No.: 14/827,544

(22) Filed: Aug. 17, 2015

(65) Prior Publication Data
US 2016/0051304 A1 Feb. 25, 2016

(30) Foreign Application Priority Data
Aug. 22, 2014 (DE) .................. 10 2014 112 043

(51) Int. Cl.
*A61B 17/88* (2006.01)
*B67B 7/92* (2006.01)
*B01F 15/02* (2006.01)

(52) U.S. Cl.
CPC .......... *A61B 17/8833* (2013.01); *B67B 7/92* (2013.01); *A61B 2017/8838* (2013.01); *B01F 15/0206* (2013.01)

(58) Field of Classification Search
CPC .... A61B 17/8833; B01F 15/0206; B67B 7/92
USPC ........................................................ 366/139
See application file for complete search history.

(56) References Cited

U.S. PATENT DOCUMENTS

| 2,179,588 | A |   | 11/1939 | Dennison |
|-----------|---|---|---------|----------|
| 2,655,767 | A |   | 10/1953 | Wenner |
| 3,892,237 | A | * | 7/1975  | Steiner ............... A61M 5/2053 604/157 |
| 3,974,942 | A |   | 8/1976  | Gray et al. |
| 4,671,263 | A |   | 6/1987  | Draenert |
| 4,758,096 | A |   | 7/1988  | Gunnarsson |
| 4,973,168 | A |   | 11/1990 | Chan |

(Continued)

FOREIGN PATENT DOCUMENTS

| CN | 2014-58698 U | 5/2010 |
|----|--------------|--------|
| CN | 2019-14910 U | 8/2011 |

(Continued)

OTHER PUBLICATIONS

Notice of Reason for Rejection corresponds to Japanese Application No. 2015-16472 dated Sep. 6, 2016.

(Continued)

*Primary Examiner* — Marc C Howell
(74) *Attorney, Agent, or Firm* — Norris McLaughlin, P.A.

(57) ABSTRACT

Opening device for the opening of a monomer liquid container (1) comprising a positioning aid (6) for positioning of the monomer liquid container (1), an opening facility (8) for the opening of the monomer liquid container (1), the opening facility (8) being mobile with respect to the positioning aid (6) and/or the positioning aid (6) being mobile with respect to the opening facility (8), at least one elastically deformable energy-storing element (9) for storage of elastic energy, whereby a motion of the opening facility (8) and/or a motion of the positioning aid (6) can be driven by the elastic energy of the at least one elastically deformable energy-storing element (9).

16 Claims, 7 Drawing Sheets

(56) References Cited

U.S. PATENT DOCUMENTS

| | | |
|---|---|---|
| 5,100,241 A | 3/1992 | Chan |
| 5,344,232 A | 9/1994 | Nelson et al. |
| 5,551,778 A | 9/1996 | Hauke et al. |
| 5,586,821 A | 12/1996 | Bonitati et al. |
| 5,588,745 A | 12/1996 | Tanaka et al. |
| 5,624,184 A | 4/1997 | Chan |
| 5,997,544 A | 12/1999 | Nies et al. |
| 6,033,105 A | 3/2000 | Barker et al. |
| 6,099,510 A | 8/2000 | Ruether et al. |
| 6,709,149 B1 | 3/2004 | Tepic |
| 2003/0155381 A1 | 8/2003 | Chan |
| 2010/0329074 A1 | 12/2010 | Vogt et al. |
| 2011/0114212 A1 | 5/2011 | Greter et al. |
| 2013/0135959 A1* | 5/2013 | Vogt .................. B29B 7/28 366/139 |
| 2013/0145727 A1* | 6/2013 | Vogt .................. A61B 17/8833 53/381.1 |
| 2014/0124534 A1* | 5/2014 | Gold .................. B65D 25/08 222/129 |
| 2016/0045243 A1 | 2/2016 | Vogt et al. |

FOREIGN PATENT DOCUMENTS

| | | | |
|---|---|---|---|
| DE | 420 352 C | 10/1925 | |
| DE | 25 19 306 A1 | 11/1975 | |
| DE | 30 45 559 C2 | 10/1982 | |
| DE | 3 640 279 A1 | 6/1987 | |
| DE | 6 981 2726 T2 | 2/2004 | |
| DE | 10 2009 031178 B3 | 9/2010 | |
| DE | 10 2011 119 377 B3 | 4/2013 | |
| EP | 0 692 229 A1 | 1/1996 | |
| EP | 0 926 500 A2 | 6/1999 | |
| EP | 1 005 901 A2 | 6/2000 | |
| EP | 1 016 452 A2 | 7/2000 | |
| EP | 1 020 167 A2 | 7/2000 | |
| GB | 28 71 72 A | 11/1928 | |
| GB | 14 96724 A | 12/1977 | |
| GB | 20 91240 A | 7/1982 | |
| GB | 2090825 A * | 7/1982 | .............. B67B 7/92 |
| GB | 20 90825 B | 6/1984 | |
| JP | S57-122873 A | 7/1982 | |
| JP | 2013-539403 A | 10/2013 | |
| WO | 94/26403 A1 | 11/1994 | |
| WO | 99/67015 A1 | 12/1999 | |
| WO | 2010/012114 A1 | 2/2010 | |

OTHER PUBLICATIONS

English Translation of the Notice of Reason for Rejection corresponds to Japanese Application No. 2015-16472 dated Sep. 6, 2016.
European Search Report dated Jan. 15, 2016.
Australian Examination Report dated Feb. 11, 2016.
DE 10 2009 031178—English Abstract attached, also Published as US 2010/329074.
DE 3 640 279—English Abstract attached, also Published as U.S. Pat. No. 4,758,096.
DE 6 981 2726—English Abstract attached, also Published as U.S. Pat. No. 6,709,149.
DE 10 2011 119 377—English Translation of Abstract, also published as US 2013/135959.
DE 30 45 559—No English Abstract available, also published as GB 2090825.
DE 25 19 306—No Abstract available, also Published as U.S. Pat. No. 3,974,942.
DE 420 352—No English Abstract available—Machine English translation provided.
EP 0 692 229—English Abstract attached, also Published as U.S. Pat. No. 5,551,778.
WO 2010/012114—English Abstract attached, also Published as US 2011/114212.
German Office Action dated Jun. 24, 2015.

* cited by examiner

TENSIONED OPENING DEVICE FOR MONOMER CONTAINER

This application claims foreign priority benefit under 35 U.S.C. § 119 of German Patent Application No. 10 2014 112 043.4, filed Aug. 22, 2014.

The invention relates to an opening device for the opening of a monomer liquid container.

The invention further relates to a vacuum mixing system having an opening device of this type and to a method for the opening of a monomer liquid container.

Accordingly, the subject matter of the invention is a device for the opening of monomer liquid containers of powder-liquid polymethylmethacrylate bone cements for the production thereof. Another subject matter of the invention is a closed vacuum mixing system for the storage, mixing, and dispensing of polymethylmethacrylate bone cement.

BACKGROUND OF THE INVENTION

Polymethylmethacrylate (PMMA) bone cements are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, a radiopaquer, and the initiator dibenzoylperoxide. The polymers of the powder component are produced on the basis of methylmethacrylate and comonomers, such as styrene, methylacrylate or similar monomers by means of polymerisation, preferably by suspension polymerisation. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

PMMA bone cements can be mixed by mixing the cement powder and the monomer liquid in suitable mixing beakers with the aid of spatulas. One disadvantage of said procedure is that air inclusions may be present in the cement dough thus formed and can cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality. Bone cements mixed in a vacuum have clearly reduced porosity and thus show improved mechanical properties. A large number of vacuum cementing systems have been disclosed of which the following shall be listed for exemplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A.

Cementing systems, in which both the cement powder and the monomer liquid are already packed in separate compartments of the mixing systems and are mixed with each other in the cementing system only right before application of the cement, are a development of cementing technology. Said full-prepacked mixing systems were proposed through EP 0 692 229 A1, DE 10 2009 031 178 B3, U.S. Pat. Nos. 5,997,544 A, 6,709,149 B1, DE 698 12 726 T2, and U.S. Pat. No. 5,588,745 A.

Patent DE 10 2009 031 178 B3 discloses a closed vacuum mixing system having a two-part dispensing plunger for closure of a cement cartridge. A combination of a gas-permeable sterilisation plunger and a gas-impermeable sealing plunger is used in this context. This principle of a closed vacuum mixing system is implemented in the closed cementing system, PALACOS® PRO, made and distributed by Heraeus Medical GmbH.

In conventional vacuum mixing systems, the monomer liquid container is opened either by manual twisting of the ampoule head, such as is proposed, for example, in WO 2010/012114 A1, or by manual puncturing of monomer liquid pouches. Subsequently, the cement powder is mixed with the monomer liquid by means of manually operated mixing devices. It is expected that there will be a need for maximally simplified vacuum mixing systems in the future. These should be autonomous and work largely automatically to the extent possible.

Accordingly, it is the object of the invention to overcome the disadvantages of the prior art. Specifically, the invention is to provide an opening device for a monomer liquid container, a vacuum mixing system, and a method to the opening of a monomer liquid container, all of which enabling strongly simplified application. In this context, the monomer liquid container is to be opened within a closed system and/or a closed or closable vacuum mixing system without parts of droplets of the content possibly being released to the outside.

Accordingly, one object of the invention is to develop a device for the non-manual opening of monomer liquid containers. This means that the device, after activation, is to provide for a safe autonomous opening of the monomer liquid container. The drive of the device must not be driven by external energy sources in this context. The aim is to use a simple and storable energy source that can be integrated into a closed vacuum mixing system.

Moreover, a closed vacuum mixing system that has the opening device for the opening of the monomer liquid container integrated into it is to be developed. The vacuum mixing system is to contain a cement cartridge, in which a cement powder is stored, as well as a separate monomer liquid container, in which the monomer liquid is situated. Accordingly, the monomer liquid is stored separate from the cement powder. Any contact of the medical users with said components shall be excluded before and after the mixing of the two cement components—i.e. the cement powder and the monomer liquid. Therefore, the monomer liquid container shall be opened and the monomer liquid shall be transferred in a closed system. The cement powder must not contact the medical user either.

SUMMARY OF THE INVENTION

The objects of the invention are met by an opening device for the opening of a monomer liquid container comprising:
a) a positioning aid for positioning of the monomer liquid container;
b) an opening facility for the opening of the monomer liquid container, whereby the opening facility is supported such as to be mobile with respect to the positioning aid and/or the positioning aid is supported such as to be mobile with respect to the opening facility; and
c) at least one elastically deformable energy-storing element for storage of elastic energy, whereby a motion of the opening facility and/or a motion of the positioning aid can be driven by the elastic energy of the at least one elastically deformable energy-storing element, and the monomer liquid container can be opened by the motion of the positioning aid with the monomer liquid container and the opening facility with respect to each other.

The monomer liquid container can be part of the opening device or the invention can provide that the monomer liquid container needs to be inserted into the opening device in order to open it with the opening device. Preferably, a monomer liquid is present in the monomer liquid container. The positioning aid only serves to keep or push the monomer liquid container into a position appropriately such that it can be opened by means of the opening facility without the monomer liquid container becoming deformed or moved due to the force exerted by the opening facility to the effect that it is not being opened. The elastic energy can simply be used to directly move the opening facility and/or the monomer liquid container. It is also feasible to provide a transmission or a rod assembly or the like for transmission of the elastic force to the opening facility and/or to the positioning aid.

Preferably, the opening device is pushed against the monomer liquid container and opens it if the force transmitted by the elastic energy-storing element via the opening facility to the monomer liquid container is large enough to break open, fracture, cut open, perforate, puncture or generally open the container. Accordingly, in theory, the monomer liquid container can be opened by tearing it open by attaching the opening facility to the container and pulling it away from the monomer liquid container to open the container. This can be affected, for example, by means of tension springs that are attached to the monomer liquid container such that they can tear it open.

DETAILED DESCRIPTION

Opening devices according to the invention can be provided such that the opening device comprises a vessel for accommodation of the monomer liquid container, in particular a closed or closable vessel for accommodation of the monomer liquid container, whereby the positioning aid is preferably arranged on the inside of the vessel, particularly preferably is arranged on an internal wall of the vessel.

Said device being as described it can be ensured that no monomer liquid inadvertently exits from the opened monomer liquid container and reaches the surroundings. In this context, the opening device and/or the energy-storing element can just as well be situated outside of the vessel and outside of the closed or closable vessel. For this purpose, the vessel preferably comprises a deformable wall by means of which a force can be transmitted into the inside of the vessel to the monomer liquid container.

Moreover, the invention can provide the monomer liquid container to be an ampoule, in particular a glass ampoule, that can be or is positioned, in particular can be or is held, by means of the positioning aid, whereby the opening facility preferably is a fracturing facility that fractures or breaks open the ampoule, in particular breaks off or breaks open an ampoule head of the ampoule, in order to open the ampoule.

To render the breaking open or fracturing of the ampoule easier, at least one predetermined breakage site can be provided on the ampoule. The fracturing facility can be provided as a pestle with a blunt end or with an edge. The monomer liquid can be stored particularly long and durably in ampoules of this type.

Moreover, the invention can just as well provide an ampoule holder to be arranged on the vessel by means of which the ampoule is or can be affixed.

As a result, a compact design can be implemented and the stability of the vessel can be used to bracket and stabilise the ampoule holder.

Moreover, the invention can provide the vessel to comprise a space for accommodation of an ampoule head of the ampoule, whereby said space possesses at least one mechanically deformable wall against which the ampoule head rests or in close proximity to which the ampoule head is situated, whereby the opening facility driven by the elastic energy deforms the mechanically deformable wall appropriately such that the ampoule head breaks off or breaks open, whereby preferably at least one liquid-permeable sieve element or filter element is provided that is arranged in the space in order to retain the ampoule head and/or fragments of the ampoule below the ampoule head.

The ampoule head is situated in close proximity to the elastic deformable wall if the deviation of the deformable wall caused by the opening facility is sufficient to break off or break open the ampoule head. Preferably, the ampoule head is situated at a distance of no more than 25 mm from the elastic wall, particularly preferably is situated at a distance of no more than 10 mm from the elastic wall, even more particularly preferably is situated at a distance of no more than 5 mm from the elastic wall. By this means, a completely closed system is provided, in which the monomer liquid contacts only the inside of the vessel and any egress of monomer liquid can be prevented reliably. The collecting of broken off fragments of the ampoule removes interfering chips. By this means, even a glass ampoule can be used as monomer liquid container without any danger.

A refinement of the present invention proposes the opening facility to be a pestle that is supported appropriately such that it is linearly mobile, and that the linear motion of the pestle can be driven by the elastic energy of the at least one elastically deformable energy-storing element.

A monomer liquid container that is easy to break open can be opened easily with said pestle. The pestle can be driven particularly well by means of a spring serving as elastic energy-storing element.

According to an alternative embodiment, the invention can provide the monomer liquid container to be a film pouch that can be or is positioned, in particular can be or is held, by means of the positioning aid, whereby the opening facility preferably is a blade or a puncturing mandrel, particularly is a hollow puncturing mandrel, that cuts open the film pouch or punctures it in order to open the film pouch.

In the present variant a film pouch containing the monomer liquid is opened by cutting it open or puncturing it. This is advantageous in that the pouches can be opened very reliably very easily and requiring little energy. As before, a sieve or a filter can be arranged below the film pouch in order to collect parts of the film that come off the film pouch and to separate them from the monomer liquid.

Preferred opening facilities according to the invention can provide the at least one elastically deformable energy-storing element to be at least one spring, preferably at least one metal spring, particularly preferably selected from steel leg springs, steel leaf springs, and steel coil springs.

Springs are very well-suited as elastic energy stores since they are easy to manufacture and/or can be obtained inexpensively as mass product, and the energy stored in them is sufficient for opening the monomer liquid container. Referring to the use of a glass ampoule as monomer liquid container, it is preferred to use metal springs to obtain the somewhat larger elastic energy required to reliably break open or fracture the glass ampoule, since the spring force of said metal springs is higher. If applicable, the energy for deforming an elastic wall of the vessel may also have to be provided and the spring must therefore be dimensioned appropriately in terms of its spring force. The spring is preferred to be a coil spring. A rubber band, a gas pressure spring, a hydraulic suspension or any other elastically deformable energy store can be used just as well instead of a normal spring.

In this context, the invention can provide the at least one spring to be guided by means of a spring guidance such that the elastic spring force of the at least one spring acts in a direction that is determined by the spring guidance.

By this means, reliable opening of the monomer liquid container can be attained, since this ensures that the spring force always acts in the desired direction.

A refinement of the present invention proposes the at least one elastically deformable energy-storing element to be tensioned and, in the tensioned state, to be arrested by at least one detachable mechanical lock such that any release of the elastic energy of the at least one energy-storing element is prevented by the at least one lock, whereby the at least one lock preferably is provided as a safety catch and/or as a safety pin.

The at least one detachable mechanical lock allows the opening facility to be operated and used easily. Once the at least one lock is detached, the elastic energy from the at least one elastic energy-storing element is released and the monomer liquid container is opened. The at least one lock can be detached manually and/or can be coupled to other locks and/or can be detached fully automatically.

For ease of use of the opening facility with monomer liquids, the invention can provide a trough-shaped receptacle for the monomer liquid below the positioning aid.

The trough-shaped receptacle allows the monomer liquid to be caught and used afterwards.

The objects underlying the present invention are also met by a vacuum mixing system for the production of a cement, comprising an opening facility, in particular an opening facility according to the invention, a mixing cartridge containing a cement powder, a monomer liquid container that is positioned by means of the positioning aid, and a conduit means connecting the mixing cartridge to an opening in the region of the monomer liquid container or to the hollow mandrel or to the trough-shaped receptacle for the monomer liquid.

The vacuum mixing system of this design comprises the advantages of the monomer liquid container. These are particularly advantageous, in particular in vacuum mixing systems, due to their ease-of-use and the insensitivity to interference. Preferably, the vacuum mixing system is well-suited for the mixing of PMMA cement in a vacuum.

In this context, the invention can provide the vacuum mixing system to comprise a foot part that bears the mixing cartridge, the conduit means, and the opening facility and connects them to each other, whereby the mixing cartridge preferably is connected to the foot part in detachable manner.

By this means, the vacuum mixing system is easy to assemble and set up. Concurrently, the stability required for the opening facility is attained.

But the objects underlying the invention are also met by a method for the opening of a monomer liquid container having an opening device as described above, in which the elastic energy is taken from the at least one elastically deformed energy-storing element, whereby the elastic energy is used to drive the opening facility and/or the positioning aid such that the opening facility and/or the positioning aid exert a force on the monomer liquid container and such that the force thus exerted opens the monomer liquid container.

In this context, the invention can provide at least one locking element to keep the at least one energy-storing element in the elastically deformed state, whereby the at least one locking element is detached in order to remove the elastic energy from the at least one energy-storing element.

Moreover, the invention can provide a tensioned spring, as energy-storing element, to push on a pestle, as opening facility, and/or a tensioned spring, as energy-storing element, to push on the positioning aid or on an ampoule, as monomer liquid container, whereby the spring pushes the pestle against the ampoule and/or the ampoule against the pestle, whereby the force thus exerted on the ampoule is used to open the ampoule, in particular in order to break open or fracture the ampoule.

Alternatively, the invention can provide a tensioned spring, as energy-storing element, to push on the opening facility by means of an edge, by means of a blade or by means of a mandrel, in particular by means of a hollow mandrel, as opening facility, and/or a tensioned spring, as energy-storing element, to push on the positioning aid or on a film pouch, as monomer liquid container, whereby the spring pushes the edge, blade or mandrel, in particular the hollow mandrel, against the film pouch and/or the film pouch against the edge, blade or mandrel, in particular the hollow mandrel, whereby the force thus exerted on the film pouch is used to open the film pouch, preferably to slit open or puncture a wall of the film pouch.

The invention is based on the surprising finding that the relaxation of an elastically deformed energy-storing element that drives an opening facility allows an opening device and a vacuum mixing system for PMMA bone cements as well as a method for the opening of a monomer liquid container to be provided, in which no manual opening of the monomer liquid container is required and in which the energy required for opening the monomer liquid container is already stored. The opening facility and the elastic energy store allow for reliable and rapid opening of the monomer liquid container with without the acting force being too strong or too weak such as to impede the opening of the monomer liquid container. As a result, an external energy source is made superfluous. In this context, the devices according to the invention and the method according to the invention work exclusively in the absence of electrical drives or motors. The application is simplified markedly, which has a beneficial effect especially in the often hectic routines during a surgery. in this context, the design remains inexpensive and the product can therefore also be offered as a disposable article, which makes sense considering the hygienic requirements in the surgical area. Methods and devices according to the invention can be used to readily produce a PMMA bone cement. Moreover, the vacuum mixing system according to the invention is well-suited for storage of the starting components and for application of the ready-mixed bone cement.

New vacuum mixing systems, such as the vacuum mixing system according to the invention, should best work autonomously and largely automatically. For a mixing system to be autonomous and automatic, it is best if the opening facility and/or the vacuum mixing system according to the invention, after activation, opens the monomer container or containers autonomously. This is attained with the present opening device according to the invention and the vacuum mixing system according to the invention.

Devices according to the invention for the opening of monomer liquid containers are characterised in that at least one elastically deformable energy-storing element is used as energy source for the opening of monomer liquid containers.

The energy-storing element in the tensioned state is preferably arrested appropriately by at least one detachable mechanical lock by means of which a release of the energy of the energy-storing element is prevented, whereby said lock is preferably provided as a safety catch and/or as a safety pin.

Then exemplary preferred embodiment of the device according to the invention comprises the following parts:
a) an ampoule holder with a monomer liquid ampoule;
b) a space for accommodation of the ampoule head, whereby said space possesses at least one mechanically deformable wall against which the ampoule head rests or in close proximity to which it is situated;
c) at least one liquid-permeable sieve element that is arranged below the ampoule head in the space for accommodation of the ampoule head;
d) a trough-shaped receptacle for the monomer liquid below the sieve element;
e) at least one pestle with a spring receptacle;
f) at least one spring with spring guidance; and
g) at least one locking element that affixes the pestle in front of the wall of the receptacle of the ampoule head when the spring is tensioned.

In the present embodiment, the monomer liquid ampoule serves as monomer liquid container, the ampoule holder serves as positioning aid, the spring serves as elastic energy-storing element or as one of the at least two energy-storing elements, and the pestle serves as opening facility.

In an alternative embodiment, a device according to the invention comprises the following parts:
a) a film pouch containing monomer liquid;
b) a hollow puncturing mandrel supported such as to be axially mobile;
c) at least one spring that acts on the puncturing mandrel when it relaxes; and
d) at least one locking element that keeps the spring, in the tensioned state, at a distance from the puncturing mandrel.

In the present alternative embodiment, the film pouch serves as monomer liquid container, the spring serves as elastic energy-storing element or as one of at least two energy-storing elements, and the puncturing mandrel serves as opening facility. The puncturing mandrel is preferably provided as a hollow mandrel in this context.

In a further embodiment of the invention, the device comprises the following parts:
a) a film pouch containing monomer liquid;
b) a hollow puncturing mandrel;
c) a film pouch receptacle that can be moved axially towards the puncturing mandrel;
d) at least one spring that acts on the film pouch receptacle when it relaxes; and
e) at least one locking element that keeps the at least one spring, in the tensioned state, at a distance from the film pouch receptacle.

In the present second alternative embodiment, the film pouch serves as monomer liquid container, the spring serves as elastic energy-storing element or as one of at least two energy-storing elements, and the puncturing mandrel serves as opening facility. The puncturing mandrel is preferably provided as a hollow mandrel in this context. The first alternative and the second alternative can also be combined with each other such that the puncturing mandrel is driven by a first spring and the film pouch receptacle containing the film pouch is moved in opposite direction by a second spring. The two spring forces of the first and second spring acting in opposite directions allows a particularly large elastic force to be used for opening the film pouch, and/or the spring forces of the first and second spring can be selected correspondingly small and the first and the second spring can be dimensioned correspondingly small, while still ensuring that the film pouch is opened.

The scope of the invention further includes an exemplary vacuum mixing system comprising a mixing cartridge, in which cement powder is stored, a separate monomer liquid container, a conduit means that connects the monomer liquid container to the mixing cartridge in liquid-permeable manner, and a foot part (base) that is connected to the mixing cartridge and the monomer containing. The vacuum mixing system further comprises, for example, one of the three devices specified above. Accordingly, the vacuum mixing system further comprises, for example,
a) an ampoule holder with monomer liquid ampoule;
b) a space for accommodation of the ampoule head, whereby said space possesses at least one mechanically deformable wall against which the ampoule head rests or in close proximity to which the ampoule head is situated;
c) at least one liquid-permeable sieve element that is arranged below the ampoule head in the space for accommodation of the ampoule head;
d) at least one pestle with a spring receptacle;
e) at least one spring with spring guidance; and
f) at least one locking element that affixes the pestle in front of the wall of the receptacle of the ampoule head when the spring is tensioned, or
a) a film pouch containing monomer liquid, as monomer container;
b) a hollow puncturing mandrel supported such as to be axially mobile;
c) at least one spring that acts on the puncturing mandrel when it relaxes; and
d) at least one locking element that keeps the spring, in the tensioned state, at a distance from the puncturing mandrel.

The scope of the invention includes, for example, a method for the opening of a monomer liquid container by means of the device according to the invention. Said method can be characterised, for example, in that
a) the locking element is detached first;
b) then the spring moves the pestle onto the deformable wall of the space for accommodation of the ampoule head;
c) the wall is deformed in the direction of the ampoule head by the action of the pestle;
d) the deformed wall breaks off the ampoule head; and
e) the monomer liquid leaks from the ampoule and flows through the sieve element into the receptacle for the monomer liquid to be passed on into the mixing cartridge.

A further alternative method containing the device according to the invention is characterised, for example, in that
a) the locking element is detached first;
b) the at least one spring relaxes;
c) the relaxing spring acts on the puncturing mandrel:
d) the puncturing mandrel punctures through the wall of the film pouch containing monomer liquid; and
e) the monomer liquid flows through the hollow puncturing mandrel in the direction of the mixing cartridge.

BRIEF DESCRIPTION OF THE DRAWINGS

Further exemplary embodiments of the invention shall be illustrated in the following on the basis of seven schematic figures, though without limiting the scope of the invention. In the figures:

FIGS. 1 and 2 showed schematic cross-sectional views of an opening device according to the invention in the locked state (FIG. 1) and in the unlocked state (FIG. 2) as part of a vacuum mixing system.

Figure 1:
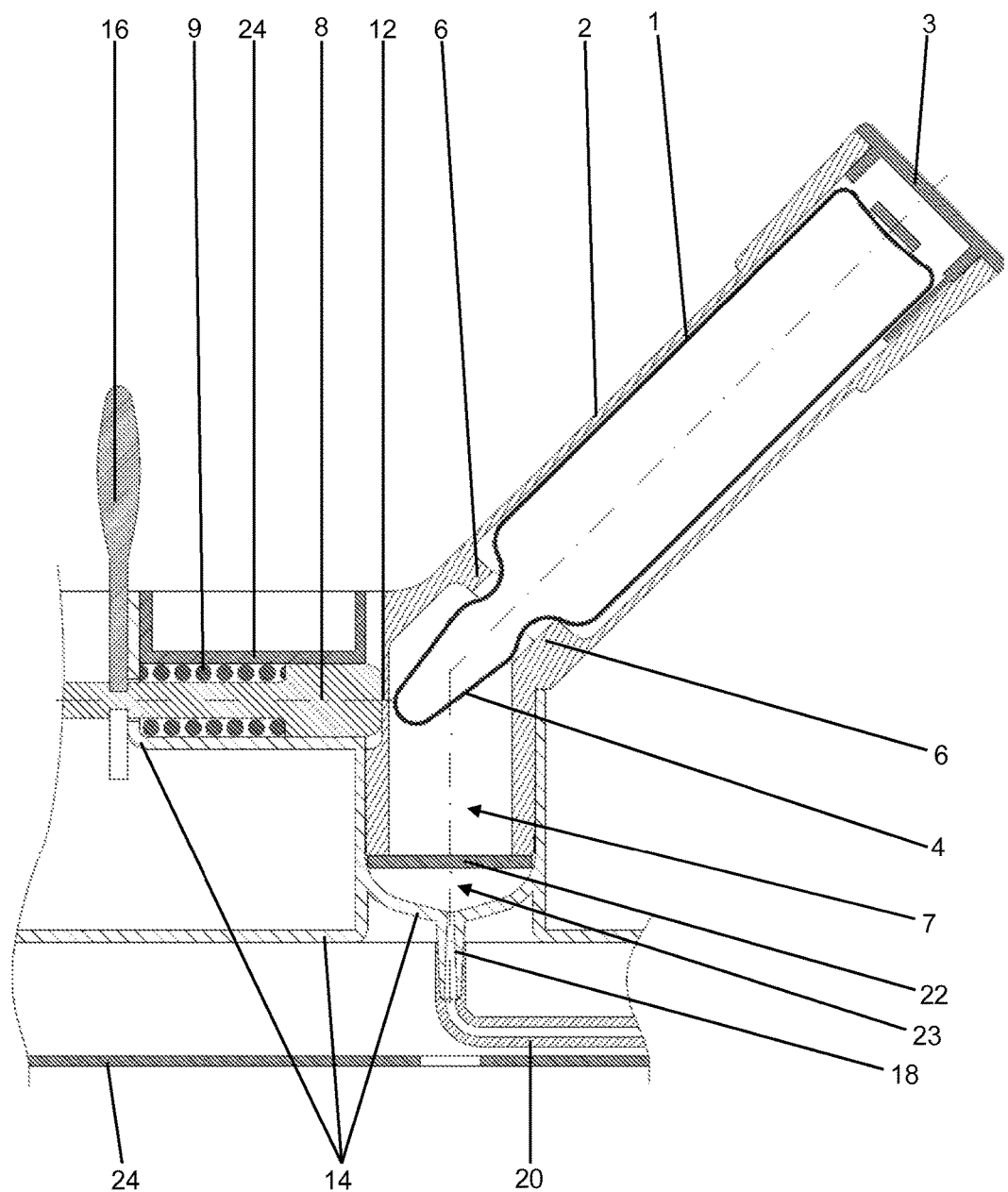
FIG. 1: shows a schematic cross-sectional view of an opening device according to the invention in the locked state.
Figure 2:
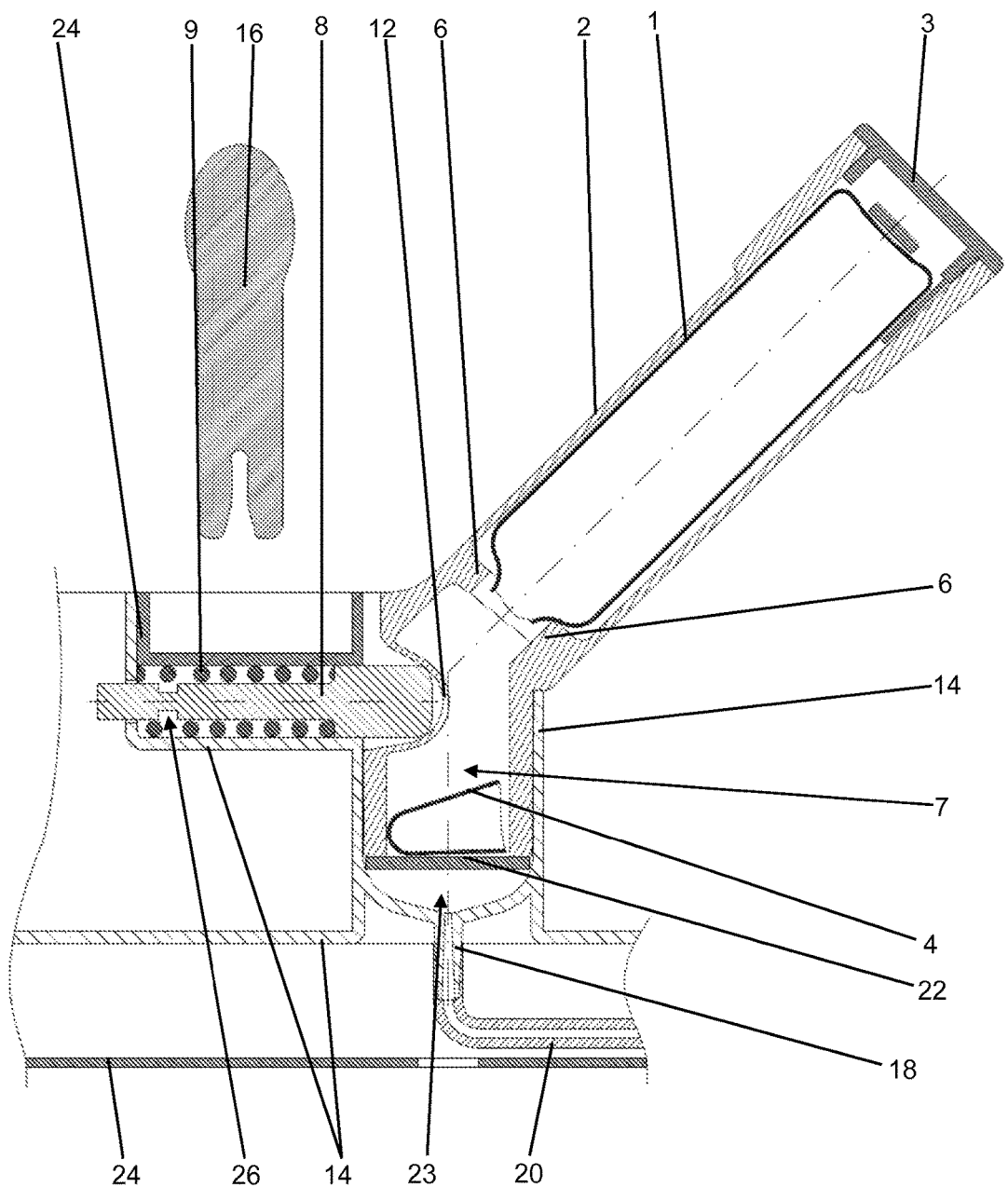
FIG. 2: shows a schematic cross-sectional view of the opening device according to the invention according to FIG. 1 in the unlocked state.

A glass ampoule 1 that can be opened by the opening device is arranged in the opening device. The glass ampoule 1 contains a liquid monomer as starting component for the production of a PMMA cement. Accordingly, the glass ampoule 1 is a monomer liquid container 1. In order to open it, the glass ampoule 1 is plugged into a vessel 2 that is closed in fluid-tight manner by a lid 3 in the way of a stopper. An ampoule head 4 of the glass ampoule 1 is inserted through a bracketing 6 that is formed by a thickening of the material of the vessel 2. The bracketing 6, but also the design of the vessel 2 and of the lid 3, affixes the glass ampoule 1 inside the vessel 2. The ampoule head 4 is broken open and/or broken off in order to open the glass ampoule 1. A space 7 for collecting the broken-off ampoule head 4 is provided below the ampoule head 4 in the vessel 2.

The ampoule head 4 can be broken off with a pestle 8 that can be propelled in the direction of the ampoule head 4 by a spring 9 made of metal or a plastic material. The pestle 8 and the spring 9 are arranged outside the vessel 2. To allow the force of the pestle 8 required to break-off the ampoule head 4 to be transmitted to the ampoule head 4, a deformable wall 12 is provided on the vessel 2, between the pestle 8 and the ampoule head 4 and/or the glass ampoule 1. Presently, the wall 12 can be deformed since it has a lower thickness. When the pestle 8 is propelled by the spring 9 in the direction of the ampoule head 4, the wall 12 deforms and the ampoule head 4 is broken off the body of the glass ampoule 1 and is thus opened. The broken-off ampoule head 4 drops into the space 7 and the content of the glass ampoule 1 (the monomer liquid) leaks from the ampoule 1.

The spring 9 is supported against a projection of the pestle 8 and against a frame 14 made of plastic material, whereby the frame 14 forms the main body of the opening device. In FIG. 1, the spring 9 is tensioned. The spring 9 and the pestle 8 are locked in FIG. 1 by a safety pin 16, as lock 16, being inserted into a recess 26 in the pestle 8 such that the safety pin 16 arrests any motion of the pestle 8, and the safety pin 16 is pulled against the frame 14 by the pestle 8.

The space 7 ends in a socket 18 in the form of a tube section onto which a conduit 20 in the form of a hose 20 is plugged. In vacuum mixing systems, the conduit 20 is connected to a mixing cartridge (not shown), in which a cement powder is arranged. The monomer liquid from the opened glass ampoule 1 can be guided through said conduit 20 to the mixing cartridge by applying a vacuum to the mixing cartridge such that the monomer liquid is aspirated from the vessel 2 through the conduit 20 into the mixing cartridge. The monomer liquid can then be mixed with the cement powder from the mixing cartridge by means of a mixing device (not shown) in the mixing cartridge in a vacuum in order to produce a PMMA cement.

A sieve 22 or a filter 22 is provided below the ampoule head 4 to prevent the broken-off ampoule head 4 from blocking the feed line through the tube socket 18 and thus to prevent glass fragments of the glass ampoule 1 from entering the PMMA cement to be mixed. Below the sieve 22 or filter 22, the space 7 is shaped in the way of a funnel as a collecting trough 23 in order to collect the monomer liquid and guided into the tube socket 18.

The vacuum mixing system comprises a base 24 and/or a foot part 24 that is firmly connected to the frame 14 or the frame 14 is a part of the foot part 24. The foot part 24 serves in the set-up of the vacuum mixing system and supports the opening device with the glass ampoule 1 and also the mixing cartridge and the conduit 20.

The monomer liquid can be stored in the closed glass ampoule 1 even over extended period of times without any problems. The glass ampoule 1 is opened briefly before the mixing with the cement powder. To open the glass ampoule 1, the safety pin 16 simply needs to be pulled out of the opening device and/or the foot part 24. The spring 9 then drives the pestle 8. Propelled in the direction of the ampoule head 4, the pestle 8 deforms the wall 12 and breaks off the ampoule head from the ampoule body of the glass ampoule 1. The monomer liquid leaks from the glass ampoule 1 through the filter 22 or the sieve 22 and accumulates in the collecting trough 23. From there, the monomer liquid can be aspirated through the tube socket 18 and the conduit 20 into the mixing cartridge by means of a vacuum in the mixing cartridge. In this location, the monomer liquid can then be mixed with the cement powder in the mixing cartridge in order to produce and/or mix the PMMA cement.

The pestle 8 also forms a spring guide for the spring 9. The frame 14 and the foot part 24 can also contribute to the guidance of the spring 9.

Figure 3:
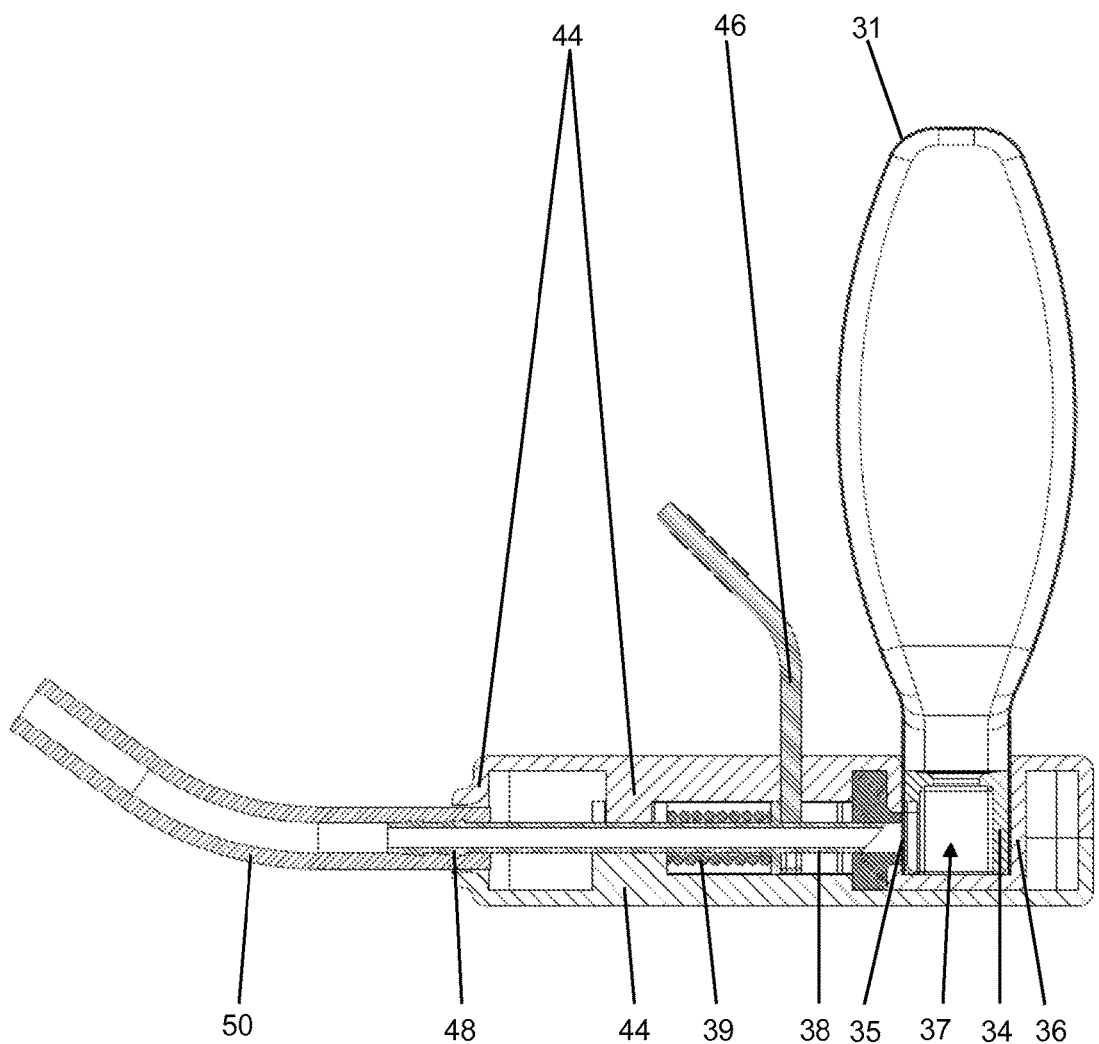
FIG. 3: shows a schematic cross-sectional view of an alternative opening device according to the invention in the locked state.
Figure 4:
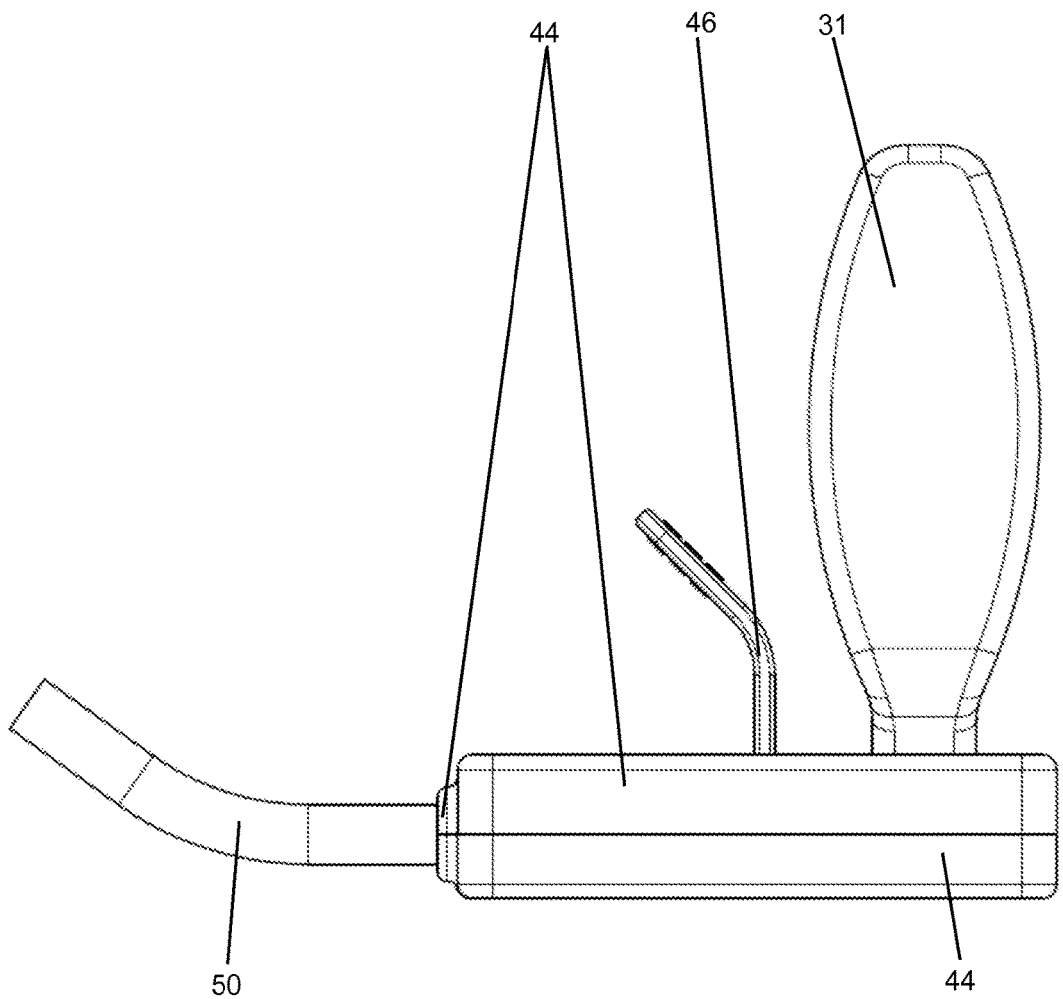
FIG. 4: shows a perspective side view of the locked opening device according to FIG. 3.
Figure 5:
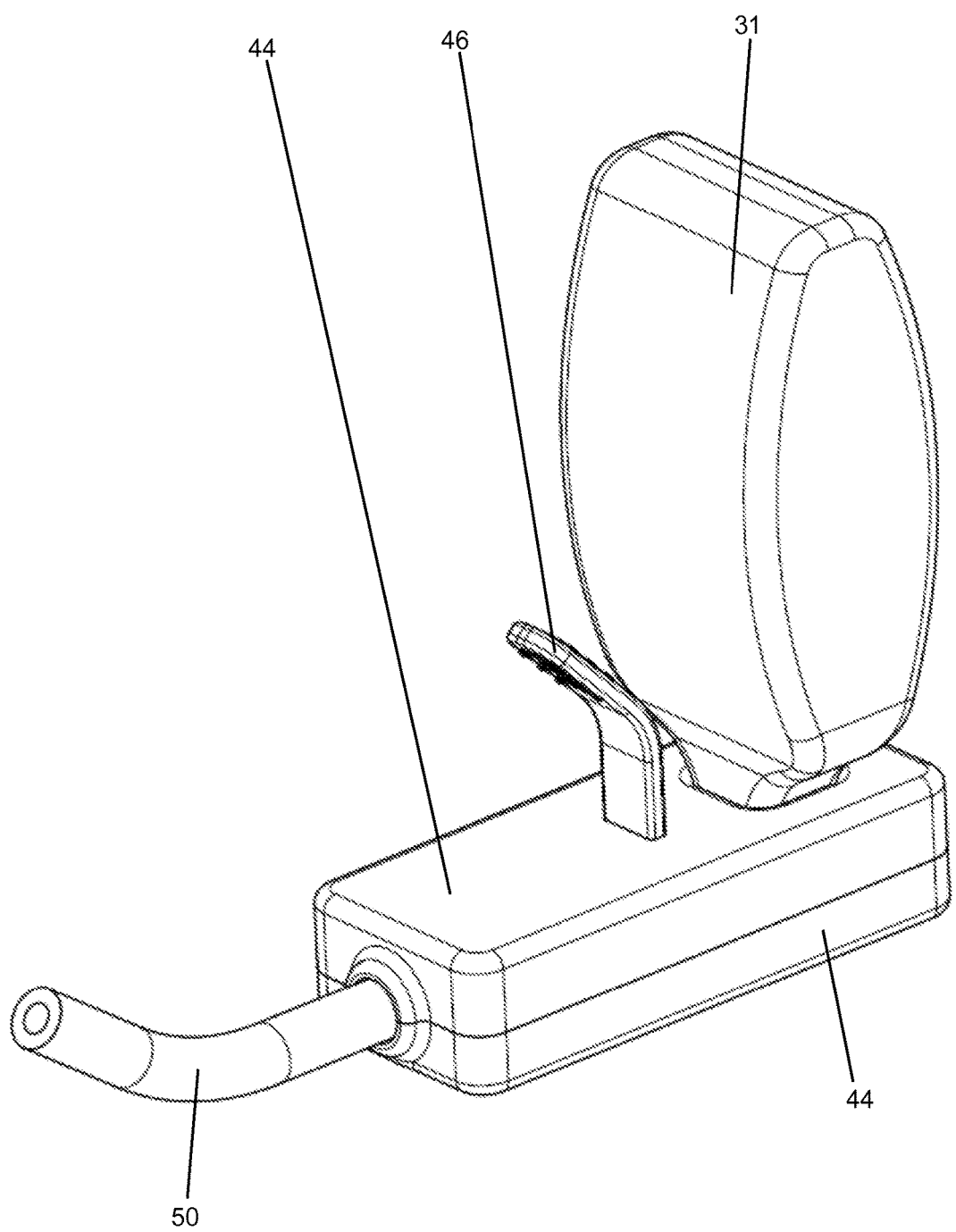
FIG. 5: shows a perspective view of the locked opening device according to FIG. 3.
Figure 6:
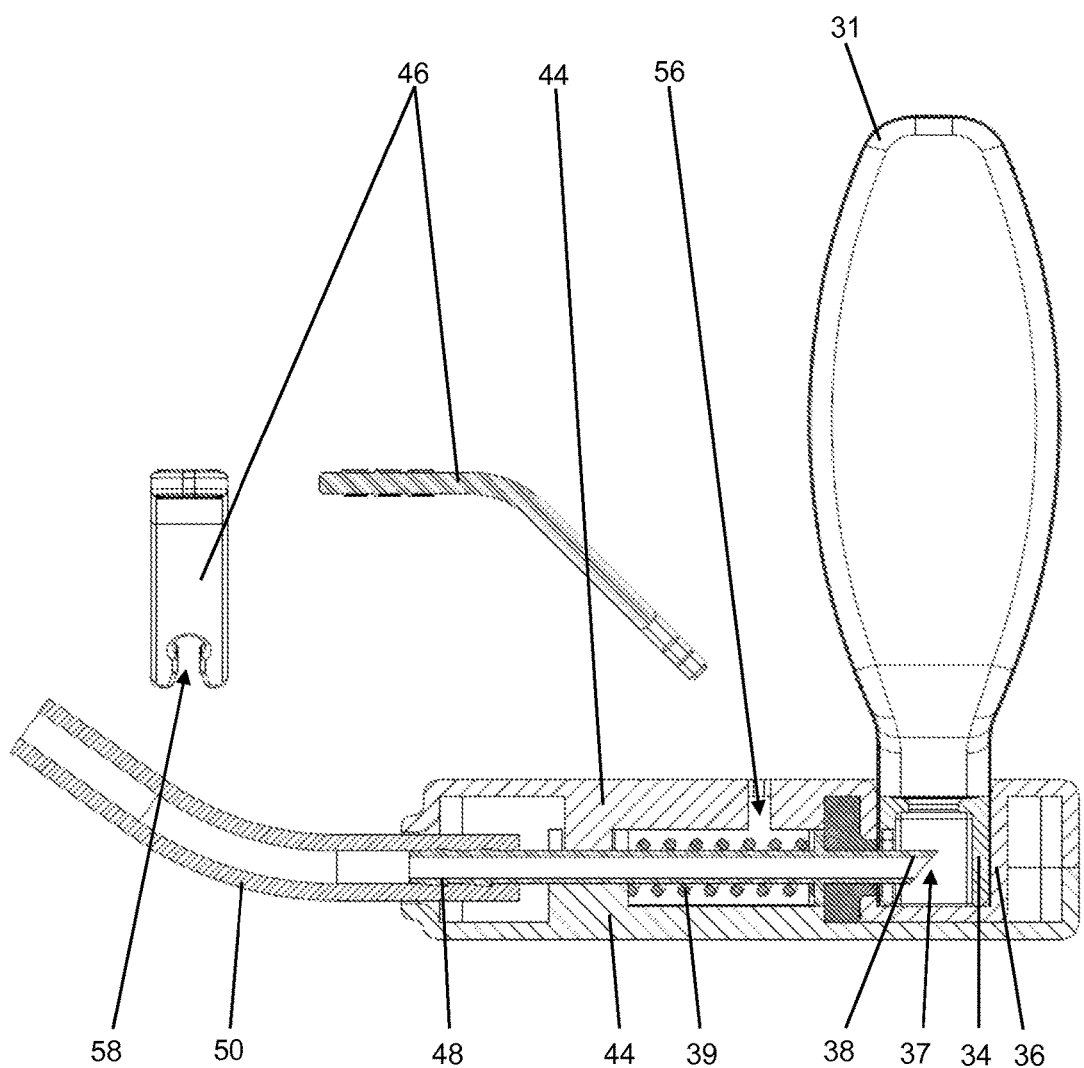
FIG. 6: shows a schematic cross-sectional view of the alternative opening device according to the invention according to FIG. 3 in the unlocked state.

FIGS. 3 to 6 show different views of an alternative opening device according to the invention. In this context, FIG. 3 shows a schematic cross-sectional view of an alternative opening device according to the invention in the locked state; FIG. 4 shows a perspective side view of the locked opening device according to FIG. 3;

FIG. 5 shows a perspective view of the locked opening device according to FIG. 3; and FIG. 6 shows a schematic cross-sectional view of the opening device according to FIG. 3 in the unlocked state.

A film pouch 31 comprising a film pouch head 34 with a plastic body is inserted into the opening divorce. The plastic body of the film pouch head 34 has recess is provided in it of which one is covered by the film 35 of the film pouch 31. The film pouch head 34 fits perfectly into a recess of a bracketing 36 of the opening device, which is also made from plastic material and is intended for this purpose. The inside of the plastic body of the film pouch head 34 forms a space 37 that is permeable he connected to the remainder of the film pouch 31. The film pouch 31 is filled with a monomer liquid and thus forms a monomer liquid container 31.

A hollow mandrel 38 is provided as opening facility 38 right next to the film 35 that covers the opening of the film pouch head 34. For this purpose, the hollow mandrel 38 is arranged opposite from the film pouch head 34 such as to be mobile in longitudinal direction (mobile from left to right in FIGS. 3 and 6). A ring disc onto which a tensioned spring 39 and/or compression spring 39, as elastic energy-storing element 39, pushes is attached to the hollow mandrel 38. On the opposite side, the spring 39 rests on a projection that is formed by a housing 44 made of plastic material. In the locked state, the spring 39 is arrested by a lock 46 that is plugged through a recess 56 in the housing 44 and engages the ring disk on the hollow mandrel 38 and thus arrests any motion of the hollow mandrel 38. The lock 46 can simply be pulled out of the recess 56 (as shown in FIG. 6) in order to unlock the opening device and/or the hollow mandrel 38 that is driven by the spring 39.

On the side facing away from the film pouch 31, the hollow mandrel 38 ends in a tube socket 48 onto which a flexible hose 50 is plugged as conduit means 50. The hollow mandrel 38, the tube socket 48, and the hose 50 are arranged in the housing 44 such as to be linearly mobile. The lock 46 comprises a recess 58 that can reach around the hollow mandrel 38 and/or the tube extending from it such that the lock 46 can snap-in with the tube and/or the hollow mandrel 38. To be able to see this, FIG. 6 shows an additional lock 46 rotated by 90°. The tube that ends in the tube socket 48 on the one side and in the hollow mandrel 38 on the other side also forms a guidance for the spring 39.

Pulling the lock 46 out of the housing, the hollow mandrel 38 is accelerated in the direction of the film 35 of the film pouch 31 by the spring 39. The slanted tip of the hollow mandrel 38 punctures through the film 35 and/or cuts open the film 85. The monomer liquid from the film pouch 31 can then flow into the hollow mandrel and the adjoining conduit 48, 50. The other end of the hose 50 can be connected to a mixing cartridge (not shown), in which a cement powder is situated, in order to form a vacuum mixing system. When the monomer liquid is supplied, the cement powder can be mixed with the monomer liquid to form a PMMA cement. A negative pressure and/or a vacuum in the mixing cartridge can be used to aspirate the monomer liquid through the hollow mandrel 38 and the adjoining conduits 48, 50 into the mixing cartridge.

Figure 7:
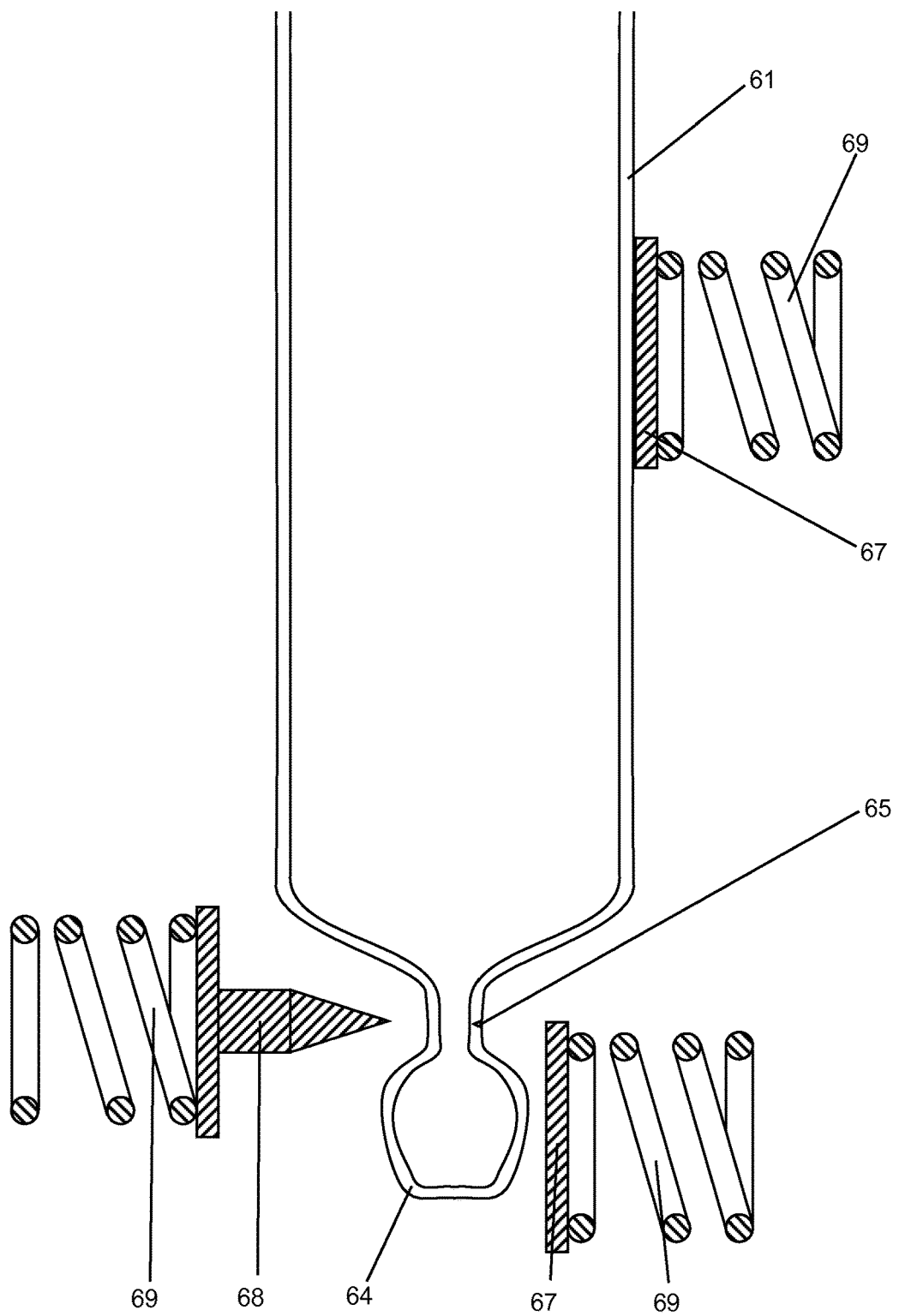
FIG. 7: shows a schematic cross-sectional view of a further alternative opening device.

FIG. 7 shows a schematic cross-sectional view of a further opening device according to the invention. An ampoule 61 made of a fragile material is arranged in the opening device. The ampoule 61 has an ampoule head 64 and an ampoule body 61 and is filled with a monomer liquid. The ampoule neck between the ampoule head 64 and the ampoule body 61 comprises a predetermined breakage site 65 such that the ampoule head 64 is easy to break off the ampoule body 61.

The opening device comprises two plates 67 and a pestle 68 with an edge. The plates 67 connected to tensioned compression springs 69 and a pestle 68 is connected to a tensioned compression spring 69. In this context, the plates 67 can be interpreted to be a mobile positioning aid 67 for the ampoule 61 and the ampoule head 64. The pestle 68 can be interpreted to be a mobile opening facility 68. This separation into positioning aid 67 and opening facility 68 may not be found, impeccably and without further ado, in all conceivable embodiments according to the invention. However, the underlying principle is obvious to a person skilled in the art, namely that the elastic energy stores 69 can be used to drive both the monomer liquid container 61 (and/or the positioning aid 67 with the monomer liquid container 61 attached to it) and the opening facility 68 against each other.

The springs 69 are kept in the tensioned position by means of a lock (not shown) or by means of three mutually independent locks (not shown). When the lock and/or locks are detached, the neck of the ampoule 61 is pushed onto the edge of the pestle 68 and the pestle 68 is pushed against the neck of the ampoule 61. As a result, the ampoule 61 breaks at the predetermined breakage site 65 and the ampoule 61 is thus being opened. The monomer liquid contained in the ampoule 61 leaks out (downwards in FIG. 7) and can be used to mix a PMMA bone cement. For this purpose, the springs 69 are held in position by a matching housing (not shown) and the plates 67 and the pestles 68 are arranged such as to be mobile with respect to the housing and are simply arrested by means of the lock. A collecting trough (not shown) for collecting the leaking monomer liquid can be arranged below the ampoule 61. Preferably, the collecting trough is connected to a conduit means (not shown) that guides the monomer liquid to a mixing space (not shown) containing a cement powder.

The features of the invention disclosed in the preceding description and in the claims, figures, and exemplary embodiments, can be essential for the implementation of the various embodiments of the invention both alone and in any combination.

LIST OF REFERENCE NUMBERS

1 Glass ampoule/monomer liquid container
2 Vessel
3 Lid
4 Ampoule head
6 Bracketing
7 Space for collecting the ampoule head
8 Pestle/opening facility
9 Spring/elastic energy-storing element
12 Deformable wall
14 Frame
16 Safety pin/lock
18 Tube socket
20 Conduit/conduit means
22 Sieve/filter
23 Collecting trough
24 Base/foot part
26 Recess
31 Film pouch/monomer liquid container
34 Film pouch head
35 Film
36 Bracketing
37 Space in the film pouch head
38 Hello mandrel/opening facility
39 Spring/elastic energy-storing element
44 Housing
46 Lock
48 Tube socket
50 Hose/conduit means
56 Recess
58 Recess
61 Ampoule
64 Ampoule head
65 Predetermined breakage site
67 Plate/opening facility
68 Pestle with edge/opening facility
69 Spring

The invention claimed is:

1. Opening device for the opening and draining of a monomer liquid container (1, 31, 61), comprising:
   a positioning aid (6, 36, 67) for positioning of the monomer liquid container (1, 31, 61) in a downwardly inverted configuration, and a receptacle for monomer liquid below the positioning aid;
   an opening facility (8, 38, 68) for the opening of the monomer liquid container (1, 31, 61), whereby the opening facility (8, 38, 68) is supported such as to be mobile with respect to the positioning aid (6, 36, 67) and/or the positioning aid (6, 36, 67) is supported such as to be mobile with respect to the opening facility (8, 38, 68); and
   at least one elastically deformable energy-storing element (9, 39, 69) for storage of elastic energy, whereby a motion of the opening facility (8, 38, 68) and/or a motion of the positioning aid (6, 36, 67) can be driven by the elastic energy of the at least one elastically deformable energy-storing element (9, 39, 69), and the monomer liquid container (1, 31, 61) can be opened by the motion of the positioning aid (6, 36, 67) with the monomer liquid container (1, 31, 61) and the opening facility (8, 38, 68) with respect to each other, whereby monomer liquid contained within said monomer liquid container can drain into said receptacle,
wherein the vessel (2) comprises a space (7) for accommodation of an ampoule head (4, 64) of the ampoule (1, 61), whereby said space (7) possesses at least one mechanically deformable wall (12) against which the ampoule head (4, 64) rests or in close proximity to which the ampoule head is situated, whereby the opening facility (8, 38, 68) driven by the elastic energy deforms the mechanically deformable wall (12) appropriately such that the ampoule head (4, 64) breaks off or breaks open, whereby at least one liquid-permeable sieve element (22) or filter element (22) is provided that is arranged in the space (7) in order to retain the ampoule head (4, 64) and/or fragments of the ampoule (1, 61) below the ampoule head.

2. Opening device according to claim 1, wherein the opening device comprises a closed or closable vessel (2) for accommodation of the monomer liquid container (1, 31, 61), whereby the positioning aid (6, 36, 67) is optionally arranged on the inside of the vessel (2).

3. Opening device according to claim 2, wherein the monomer liquid container (1, 31, 61) is an ampoule (1, 61) that can be or is positioned by means of the positioning aid (6, 36, 67), whereby the opening facility (8, 38, 68) is a fracturing facility (8, 68) that fractures or breaks open the ampoule (1, 61).

4. Opening device according to claim 3, wherein an ampoule holder (6) is arranged on the vessel (2) by means of which the ampoule (1, 61) is or can be affixed.

5. Opening device according to claim 1, wherein the opening facility (8, 38, 68) is a pestle (8, 68) that is supported appropriately such that it is linearly mobile, and the linear motion of the pestle (8, 68) can be driven by the elastic energy of the at least one elastically deformable energy-storing element (9, 39, 69).

6. Opening device according to claim 1, wherein the monomer liquid container (1, 31, 61) is a film pouch (31) that can be or is positioned by means of the positioning aid (6, 36, 67), whereby the opening facility (8, 38, 68) optionally is a blade or a puncturing mandrel (38) that cuts open the film pouch (31) or punctures it in order to open the film pouch (31).

7. Opening device according to claim 1, wherein the at least one elastically deformable energy-storing element (9, 39, 69) is at least one spring (9, 31, 69).

8. Opening device according to claim 7, wherein the at least one spring (9, 39, 69) is guided by means of a spring guidance such that the elastic spring force of the at least one spring (9, 39, 69) acts in a direction that is determined by the spring guidance.

9. Opening device according to claim 1, wherein the at least one elastically deformable energy-storing element (9, 39, 69) is tensioned and, in the tensioned state, is arrested by at least one detachable mechanical lock (16, 46) such that any release of the elastic energy of the at least one energy-storing element (9, 39, 69) is prevented by the at least one lock (16, 46), whereby the at least one lock (16, 46) is provided as a safety catch and/or as a safety pin (16, 46).

10. Opening device according to claim 1, wherein said receptacle is a trough-shaped receptacle.

11. Vacuum mixing system for the production of a cement, comprising an opening facility according to claim 1, a mixing cartridge containing a cement powder, a monomer liquid container (1, 31, 61) that is positioned by means of the positioning aid (6, 36, 67), and a conduit (20, 50) connecting the mixing cartridge to an opening in the region of the monomer liquid container (1, 31, 61).

12. Vacuum mixing system according to claim 11, wherein the vacuum mixing system comprises a foot part (24) that bears the mixing cartridge, the conduit (20, 50), and the opening facility and connects them to each other, whereby the mixing cartridge is connected to the foot part (24) in detachable manner.

13. Method for opening a monomer liquid container (1, 31, 61) with an opening device according to claim 1, wherein the elastic energy is taken from the at least one elastically deformed energy-storing element (9, 39, 61), whereby the elastic energy is used to drive the opening facility (8, 38, 68) and/or the positioning aid (6, 36, 67) such that the opening facility (8, 38, 68) and/or the positioning aid (6, 36, 67) exert a force on the monomer liquid container (1, 31, 61) and such that the force thus exerted opens the monomer liquid container (1, 31, 61).

14. Method according to claim 13, wherein at least one locking element (16, 46) keeps the at least one energy-storing element (9, 39, 69) in the elastically deformed state, whereby the at least one locking element (16, 46) is detached in order to remove the elastic energy from the at least one energy-storing element (9, 39, 69).

15. Method according to claim 13, wherein a tensioned spring (9, 39, 69), as energy-storing element (9, 39, 69), pushes on a pestle (8, 68), as opening facility (8, 38, 68), and/or a tensioned spring (9, 39, 69), as energy-storing element (9, 39, 69), pushes on the positioning aid (6, 36, 67) or on an ampoule (1, 61), as monomer liquid container (1, 31, 61), whereby the spring (9, 39, 69) pushes the pestle (8, 68) against the ampoule (1, 61) and/or the ampoule (1, 61) against the pestle (8, 68), whereby the force thus exerted on the ampoule (1, 61) is used to open the ampoule (1, 61).

16. Method according to claim 13, wherein a tensioned spring (9, 39, 69), as energy-storing element (9, 39, 69), pushes on the opening facility (8, 38, 68) by means of an edge, by means of a blade or by means of a mandrel (38) as opening facility (8, 38, 68), and/or a tensioned spring (9, 39, 69), as energy-storing element (9, 39, 69), pushes on the positioning aid (6, 36, 67) or on a film pouch (31), as monomer liquid container (1, 31, 61), whereby the spring (9, 39, 69) pushes the edge, blade or mandrel (38), against the film pouch (31) and/or the film pouch (31) against the edge, blade or mandrel (38), whereby the force thus exerted on the film pouch (31) is used to open the film pouch open 131).

* * * * *